United States Patent [19]

Dancsi et al.

[11] 4,410,459
[45] Oct. 18, 1983

[54] PROCESS FOR PREPARATION OF CYTOSTATIC COMPOUNDS

[75] Inventors: Lajos Dancsi; Tibor Keve; Lajos Szabó; Katalin Honty; Sándor Eckhardt; Iván Hindi; Sándor Kerpel-Fronius; György Fekete; Eszter Dezséri; Sándor Görög; Tibor Ács; Csaba Szántay; Zsuzsanna Relle neé Somfai; János Sugár, all of Budapest, Hungary

[73] Assignee: Richter Gedeon Vegyeszeti Gyar Rt., Budapest, Hungary

[21] Appl. No.: 293,611

[22] Filed: Aug. 17, 1981

[30] Foreign Application Priority Data

Oct. 22, 1980 [HU] Hungary ..................... 2563

[51] Int. Cl.³ .................. C07D 519/04; A61K 31/475
[52] U.S. Cl. .................................... 260/244.4; 424/262
[58] Field of Search ...................... 260/244.4; 424/262

[56] References Cited

U.S. PATENT DOCUMENTS

| | | | |
|---|---|---|---|
| 4,075,214 | 2/1978 | Katner et al. ............... | 260/244.4 |
| 4,143,041 | 3/1979 | Thompson ..................... | 260/244.4 |
| 4,298,525 | 11/1981 | Jovanovics et al. ........ | 424/262 |
| 4,310,528 | 1/1982 | Jovanovics et al. ........ | 424/262 |

FOREIGN PATENT DOCUMENTS

| | | | |
|---|---|---|---|
| 18231 | 10/1980 | European Pat. Off. . | |
| 2049677 | 12/1980 | United Kingdom ........... | 424/262 |

OTHER PUBLICATIONS

Jovanovics, et al., Chemical Abstracts, vol. 95, 25380y (1981).
Helferich, et al., Chem. Berichte, 56, pp. 766–771 (1923).
Pratt, et al., J. Am. Chem. Soc., 71, pp. 2846–2849 (1949).

*Primary Examiner*—Diana G. Rivers
*Attorney, Agent, or Firm*—Karl F. Ross; Herbert Dubno

[57] ABSTRACT

The invention relates to new cytostatic compound, process for their preparation and pharmaceutical compositions containing them. More particularly, there are provided new compounds of the general formula

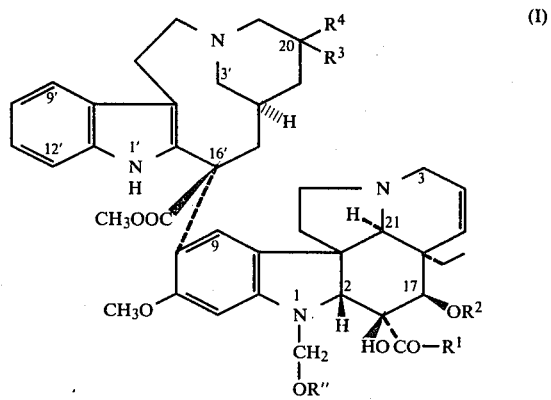

in which
$R^4$ is $\beta$-hydroxyl and
$R^3$ is $\alpha$-ethyl; or
$R^4$ is hydrogen and
$R^3$ is $\beta$-ethyl;
R" is a straight chained alkyl having from 1 to 10 carbon atoms, or a branched chained alkyl having from 3 to 10 carbon atoms, in which groups the carbon atom attached to the $>N_a\text{-}CH_2\text{-}O-$ group has a primary or secondary configuration or an alkenyl or alkinyl having from 3 to 6 carbon atoms, or an aralkyl having from 1 to 3 carbon atoms in the alkyl moiety;
$R^1$ is methoxy and
$R^2$ is acetyl,
provided that if $R^3$ is $\alpha$-ethyl and $R^4$ $\beta$-hydroxyl, $R^4$ is other than ethyl.

These compounds and N-desmethyl-N-ethoxy-methyl-vinblastine can be prepared according to the invention by transetherification of compounds of the compounds of the general formula

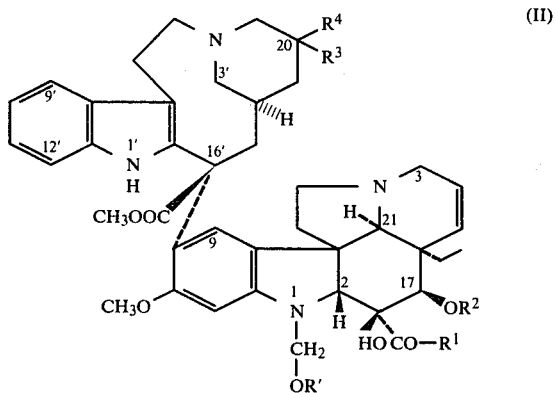

with a large excess of alcohols of the general formula

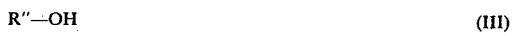

Pharmaceutical compositions containing compounds of the general formula (I) as active ingredients are also within the scope of invention.

6 Claims. No Drawings

PROCESS FOR PREPARATION OF CYTOSTATIC COMPOUNDS

The invention relates to new cytostatic compounds, process for their preparation and pharmaceutical compositions containing them.

More particularly, the invention concerns new compounds of the formula (I)

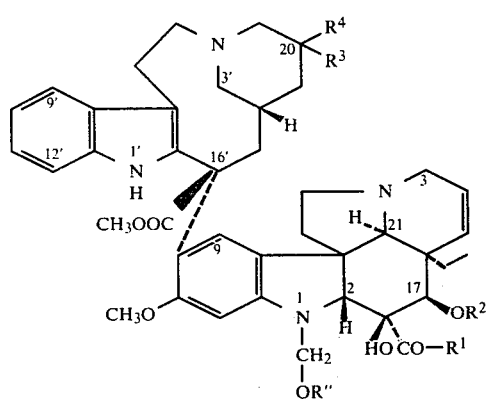

in which
R$^4$ is β-hydroxyl and
R$^3$ is α-ethyl; or
R$^4$ is hydrogen and
R$^3$ is β-ethyl;
R" is a straight chain alkyl having from 1 to 10 carbon atoms or a branched chain alkyl having from 3 to 10 carbon atoms, in which groups the carbon atom attached to the >N$_a$—CH$_2$—O— group has a primary or secondary configuration or an alkenyl or alkinyl having from 3 to 6 carbon atoms or an aralkyl having from 1 to 3 carbon atoms in the alkyl moiety;
R$^1$ is methoxy and
R$^2$ is acetyl,
provided that if R$^3$ is α-ethyl, R$^4$ is β-hydroxyl, R" is other than ethyl.

The new compounds of the formula (I), in which R$^1$, R$^2$, R$^3$, R$^4$ and R" are as defined above, show cytostatic activity.

A structurally closely related compound, N-desmethyl-N-(ethoxymethyl)-vinblastine (compound of the formula (I), in which R$^1$=methoxy, R$^2$=acetyl, R$^3$=α-ethyl, R$^4$=β-hydroxyl and R"=ethyl) and its preparation are disclosed in the/European Patent Application No. 80301290.5 (published under No. 18231). According to the process described therein N-desmethyl-N-(ethoxymethyl)-vinblastine is prepared by reacting vinblastine with chromium trioxide in a suitable solvent, in the presence of a large excess of ethanol. The reaction involved the conversion of the >N$_a$—CH$_3$ group of vinblastine to a >N$_a$—CH$_2$—O—C$_2$H$_5$ group.

In attempting to prepare further compounds of the formula (I) it has been found that only a part of the compounds of the formula (I) can be prepared following the method developed for the preparation of N-desmethyl-N-(ethoxymethyl)-vinblastine, i.e. only certain alcohols are capable of transforming the >N$_a$—CH$_3$ group of the starting compound into a corresponding >N$_a$—CH$_2$—OR" group. More particularly, we found that the required conversion could be performed with alcohols, in which R" is a straight chained alkyl with 1 to 10 carbon atoms or a branched chained alkyl with 3 to 10 carbon atoms, in which the carbon atom attached to the —OH group had a primary or secondary configuration, or in which R" represented an arylalkyl group containing from 1 to 3 carbon atoms in the alkyl moiety. Accordingly, only the compounds of the formula (I), in which R" has the above, restricted definition could be prepared by the oxidation described above. These compounds will be referred to subsequently as "compounds of the formula (I) prepared by oxidation".

It has been found that all compounds of the formula (I) described hereinabove and N-desmethyl-N-(ethoxymethyl)-vinblastine can be prepared by "transetherification" of any of the compounds of the formula (I) prepared by oxidation. The term "transetherification" is used to refer to a reaction by which the group >N$_a$—CH$_2$—OR' is converted into a group >N$_a$—CH$_2$—O—R", in the presence of a large excess of an alcohol of the formula (III) at a pH between 3 and 5.

This transetherification has the following major advantages:

1. Compounds of the formula (I), which cannot be prepared by oxidation, can be obtained.
2. Compounds, which could be prepared by a direct oxidation with a poor yield can be obtained from other compounds, which are prepared oxidatively with an excellent yield by transetherification and in this way their yield can considerably be improved. For instance the yield of N-desmethyl-N-(benzyloxymethyl)-vinblastine is doubled when this compound is prepared by the reaction:

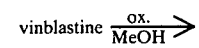

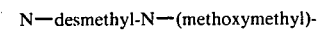

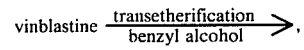

instead of direct oxidation of vinblastine, in the presence of benzyl alcohol.

According to a further feature of the present invention there is provided a process for the preparation of compounds of the formula

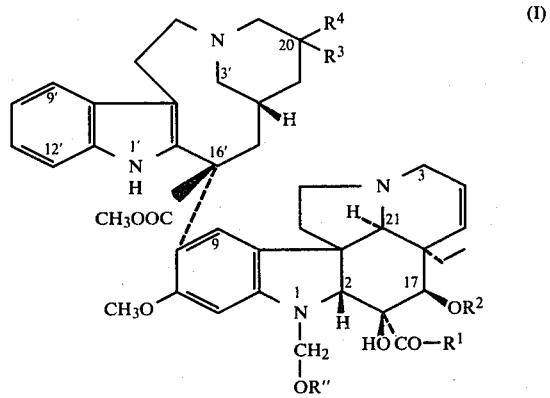

in which
R$^4$ is β-hydroxyl and
R$^3$ is α-ethyl; or

R[4] is hydrogen and
R[3] is β-ethyl;
R" is a straight chain alkyl having from 1 to 10 carbon atoms or a branched chain alkyl having from 3 to 10 atoms, in which groups the carbon atom attached to the $>N_a$—CH$_2$—O— group has a primary or secondary configuration or an alkenyl or alkinyl having from 3 to 6 carbon atoms, or cycloalkyl having from 5 to 7 carbon atoms or an aralkyl group, in which the alkyl moiety contains from 1 to 3 carbon atoms;
R[1] is methoxy and
R[2] is acetyl,
which comprises reacting a compound of the formula

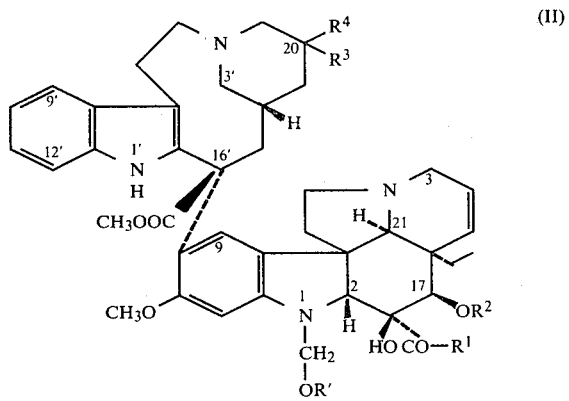
(II)

in which R[1], R[2], R[3] and R[4] are as defined hereinabove, and

R' is a straight chain alkyl having from 1 to 10 carbon atoms or a branched chain alkyl having from 3 to 10 carbon atoms, in which the carbon atom attached to the $>N_a$—CH$_2$—O— group has a primary or secondary configuration, or alkenyl having from 3 to 6 carbon atoms, alkinyl having from 3 to 6 carbon atoms, cycloalkyl having from 5 to 7 carbon atoms, or arylalkyl, in which the alkyl moiety contains from 1 to 3 carbon atoms, provided that in a starting compound of the formula (II) R' has a different meaning from R" in an end product of the formula (I) prepared therefrom, with a large excess of an alcohol of the formula

R"—OH      (III)

wherein R" has the same meaning as defined above, at a pH of 3 to 5, adjusting the pH of the reaction mixture to 7 to 8, isolating a compound of the formula (I) and optionally epimers thereof, and if desired, subjecting them to purification.

As mentioned above the new compounds of the formula (I) possess interesting pharmacological properties and, in particular, show cytostatic activity. They are less toxic than the commercially available bis-indole alkaloids, known in the art.

The acute toxicity of the compounds according to the invention was tested on male Swiss mice weighing 27 to 31 g. The tests were carried out on groups of six mice. Test compounds were administered intraperitoneally, as injectable solutions prepared with physiological saline solution and optionally one drop of Tween 80. Doses were successively increased from a dose causing no mortality up to the lethal dose. The results were evaluated by the method of Lichfield and Wilcoxon and are listed in the following Table 1.

TABLE 1

| Compound | LD$_{50}$ [mg./kg., i.p. mice] | Paralytic side effect |
| --- | --- | --- |
| N—desmethyl-N—(methoxymethyl)-vinblastine | ~100 | 0 |
| N—desmethyl-N—(ethoxymethyl)-vinblastine | ~110 | 0 |
| N—desmethyl-N—(propoxymethyl)-vinblastine | ~80 | 0 |
| N—desmethyl-N—(isobutoxymethyl)-vinblastine | ~60 | 0 |
| N—desmethyl-N—(heptoxymethyl)-vinblastine | ~60 | 0 |
| N—desmethyl-N—(allyloxymethyl)-vinblastine | ~45 | 0 |
| N—desmethyl-N—(benzyloxymethyl)-vinblastine | ~70 | 0 |
| N—desmethyl-N—(cyclohexylmethyl)-vinblastine | ~60 | 0 |
| vincristine | 4.2 | + |
| vinblastine | 7.6 | 0 |
| vindesine | 4.0 | + |

The test compounds are 15 to 25 times less toxic than vincristine and vidensine, respectively, and 8 to 13 times less toxic than vinblastine. Unlike vindesine, the test compounds did not induce any paralytic side-effect during this test.

The cytostatic effect of the new compounds was tested also in tissue cultures and various transplanted tumor strains.

The test compounds were dissolved in the tissue cultures (HeLa culture) in concentrations ranging from the threshold dose of $1 \times 10^{-3}$ μg./ml. up to 100 μg./ml. In 24-hour cultures, by in vivo microscopic evaluation of the metaphase-arresting affect the following results were obtained.

TABLE 2

| Compound | Dose inducing a strong block [μg./ml.] |
| --- | --- |
| N—desmethyl-N—(methoxymethyl)-vinblastine | 0.001 |
| N—desmethyl-N—(propoxymethyl)-vinblastine | 0.001 |
| N—desmethyl-N—(isobutoxymethyl)-vinblastine | 0.001 |
| N—desmethyl-N—(heptoxymethyl)-vinblastine | 0.001 |
| N—desmethyl-N—(allyloxymethyl)-vinblastine | 0.001 |
| N—desmethyl-N—(benzyloxymethyl)-vinblastine | 0.01 |
| N—desmethyl-N—(cyclohexyloxymethyl)-vinblastine | 0.001 |

Under similar conditions but using stained tissue cultures slight differences could be observed which can be classified as follows:

The first stage (minimal effective dose) is characterized by an increased ratio of blocked mitoses. A part is abnormal mitoses, for example three-group mitosis or polar chromosomes also occur. Generally the anaphases have already disappeared.

In the second stage a strong metaphase blocking is observed and practically there is no regulare mitosis present. Chromosomes are in the form of a loose glomus. The proportion of interphase cells is low.

In the third stage the chromosomas are aggregated in a mass in the middle of the cell. This state is called picnomitosis of "Ball-Metaphase".

In the fourth stage already the interphase cells are influenced. More particularly, the number of the blocked cells is decreased since they are not able to take part in mitosis. The cytoplasm of the cells (in interphase) is extended, its border is irregular, "fringy", the cells frequently have an elongated, fibroplast-like shape.

Finally, in the fifth stage the cytoplasm is filled in by a fine, reticular structure and the interphase cell has unambiguously been killed by the treatment.

The above stages could be well-distinguished when testing the compounds according to the invention.

The following observations were made: The most effective compound was the heptoxy derivative, which induced a strong metaphasis block even in a dose of 0.001 μg./ml. Pycnomitosis was observed at a dose of 0.1 μg./ml. while the interphase cells were influenced at doses between 1 and 10 μg./ml. The isobutoxy derivative had an order of a magnitude lower effect, namely at a dose of 0.001 μg./ml. regular mitoses could still be observed. The benzyloxy derivative had the weakest effect. At the lowest dose used this compound induced a minimum block with several deformed mitoses but without anaphases. At 0.01 μg./ml. the block was moderate and a strong block and pycnomitosis were induced only by a dose of 1 μg./ml.

The effect of the new compounds on intraperitoneally transplantable tumors (P 388 mouse leukaemia and NK/Ly ascites lymphoma) is described hereinbelow. The P 388 leukaemia test was performed on BDF hybrid mice. The tests were carried out on groups of six mice and $10^6$ tumor cells/animal were transplanted intraperitoneally. Administration of the test compounds was started in the 24th hour after transplantation. Treatment was performed intraperitoneally and the body weight and state of animals was controlled every day. The effect obtained on the treated animals is expressed in % of the mean length of life of the control group, given in days.

The results set forth in the following table show that the life span of the mice having a P 388 leukaemia is considerably increased by the test compounds.

TABLE 3

| Compound | Dose mg./kg. i.p. | Mean length of life (days) Treated | Mean length of life (days) Control | Treated/ Control (%) | Toxicity |
|---|---|---|---|---|---|
| N—desmethyl-N— (heptoxymethyl)- vinblastine | 8 × 0.4 | 14.3 | 10.3 | 139 | |
| | 8 × 4.0 | 18.7 | 10.3 | 181 | |
| | 8 × 8.0 | 21.3 | 9.9 | 247 | |
| N—desmethyl-N— (benzyloxy- methyl)-vin- blastine | 8 × 0.4 | 13.0 | 10.3 | 126 | |
| | 8 × 4.0 | 18.3 | 10.3 | 178 | |
| | 5 × 8.0 | 19.2 | 9.9 | 195 | |
| N—desmethyl-N— (isobutoxy- methyl)-vin- blastine | 8 × 0.4 | 13.7 | 10.3 | 133 | |
| | 8 × 4.0 | 20.0 | 10.3 | 194 | |
| | 8 × 8.0 | 20.5 | 9.9 | 208 | |
| N—desmethyl-N— (methoxy- methyl)-vin- blastine | 8 × 1.0 | 12.7 | 10.3 | 122 | |
| | 8 × 2.0 | 18.7; 16.8 | 10.5 | 178;155 | |
| | 8 × 4.0 | 19.0; 17.7 | 11.1 | 171;163 | |
| | 8 × 6.0 | 19.2 | 10.5 | 182 | |
| | 8 × 8.0 | 18.7 20.2 | 10.8 | 172;205 | |
| N—desmethyl-N— (propoxy- methyl)-vin- blastine | 8 × 1.0 | 15.0 | 10.3 | 145 | |
| | 8 × 2.0 | 20.8 | 10.5 | 198 | |
| | 8 × 4.0 | 19.0 | 11.1 | 171 | |
| | 8 × 8.0 | 20.2 | 9.9 | 205 | |
| | 8 × 10.0 | 14.7 | 10.3 | 142 | toxic* |
| N—desmethyl-N— (allyloxy- methyl)-vin- | 8 × 0.4 | 15.0 | 10.3 | 145 | |
| | 8 × 4.0 | 21.0 | 10.3 | 200 | |
| | 8 × 8.0 | 20.5 | 9.9 | 207 | |
| N—desmethyl-N— (cyclohexyloxy- methyl)-vin- | 8 × 0.4 | 13.1 | 10.3 | 127 | |
| | 8 × 4.0 | 18.8 | 10.3 | 181 | |
| | 8 × .8.0 | 19.3 | 9.9 | 197 | |
| N—desmethyl-N— (ethoxymethyl)- vinblastine | 8 × 2.0 | 20.3 | 10.5 | 193 | |
| | 8 × 4.0 | 18.5 | 11.1 | 167 | |
| | 8 × 8.0 | 20.5 | 9.9 | 208 | |

*The animals died tumor-free.

Into groups of ten Swiss-H/Riop outbred mice from our own breed $5 \times 10^6$ ascites tumour cells were transplanted intraperitoneally. In the 24th hour after transplantation treatment was started and the compounds were administered daily, altogether five times. The mean length of life of the control group amounted to 15.7 days.

Similar tests were performed with N-desmethyl-N-(methoxymethyl)-20'-desoxy-leurosidine. In these tests the doses and the number of treatments were varied.

The following results were obtained:

TABLE 4

| Compound | Dose (mg./kg.) i.p. | Mean length of life (days) Treated | Mean length of life (days) Control | Treated/ Control (%) |
|---|---|---|---|---|
| N—desmethyl-N— (methoxymethyl)- 20'-desoxy- leurosidine | 4 × 8 | 21.8 | 12.1 | 180 |
| | 8 × 4 | 20.8 | 11.6 | 180 |
| | 4 × 7 | 17.1 | 12.1 | 142 |
| | 8 × 1 | 21.7 | 12.2 | 178 |
| | 8 × 0.5 | 15.3 | 12.2 | 126 |

The compounds result in a considerable increase of life span as shown in the following table.

TABLE 5

| Compound | Dose mg./kg. i.p. | alive | on the 25th day tumor-free | on the 30th day tumor-free |
|---|---|---|---|---|
| N—desmethyl-N— (heptoxymethyl)- VLB | 5 × 6.0 | 10/10 | 7/10 | 3/10 |
| N—desmethyl-N— (isobutoxymethyl)- VLB | 5 × 4.0 | 10/10 | 10/10 | 7/10 |
| N—desmethyl-N— (allyloxymethyl)- VLB | 5 × 4.0 | 10/10 | 10/10 | 6/10 |
| N—desmethyl-N— (cyclohexyloxy- methyl)-VLB | 5 × 4.0 | 10/10 | 5/10 | 3/10 |

The tumor inhibitory effect of the new compounds on P 388 and NK/Ly strains is significant in a 4 to 8 mg./kg./day dose and is equal to the effect of the known diindole alkaloids. In the same time, the instant compounds are far less toxic than the known compounds having an analogous structure.

For human treatment the compounds can best be employed intravenously or as infusions.

According to the invention the compounds of the formula (I) are prepared by transetherification. As a starting compound, compounds of the formula (II) are used. It is preferred to start from compounds of the formula (II), which can be prepared by oxidation with an excellent yield.

By oxidation those compounds of the formula (II) can be prepared, in which $R^4$ is β-hydroxyl and
$R^3$ is α-ethyl; or
$R^4$ is hydrogen and
$R^3$ is β-ethyl;
R" is a straight chained alkyl having from 1 to 10 carbon atoms, a branched chained alkyl having from 3 to 10 carbon atoms, in which groups the carbon atom attached to the $>N_a$—$CH_2$—O— group has a primary or secondary configuration, or an arylalkyl group containing from 1 to 3 carbon atoms in the alkyl moiety;
$R^1$ is methoxy and
$R^2$ is acetyl.

The above compounds of the formula (II) can be prepared by the following oxidative process:

A compound of the formula

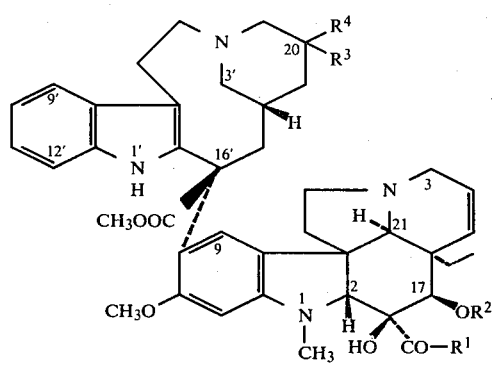

$R^1$, $R^2$, $R^3$ and $R^4$ have the same meaning as defined above, or an acid addition salt thereof is reacted with an excess amount of an alcohol of the formula (III), in which R" is a straight chain alkyl having from 1 to 10 carbon atoms or a branched chain alkyl having from 3 to 10 carbon atoms, in which groups the carbon atom attached to the OH group has a primary or secondary configuration, or R" is an arylalkyl group containing from 1 to 3 carbon atoms in the alkyl moiety, in the presence of chromium trioxide, a suitable organic solvent and acetic anhydride and an acid, at a temperature between −60° C. and −30° C., preferably between −50° C. and −60° C., adjusting the pH of the reaction mixture to 8 to 10, and isolating the product obtained, optionally after purification.

The oxidation is further illustrated by Examples 1 to 9. By the oxidative process N-desmethyl-N-(methoxymethyl)-derivatives are obtained with the best yields, therefore these are the most preferred starting compounds for the transetherification process. Transetherification is entirely reversible, i.e. from any of the compounds of the formula (II) any compounds of the formula (I) can be prepared, and vica-versa. To prove this statement the following experiments were performed:

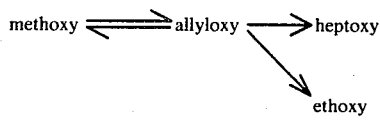

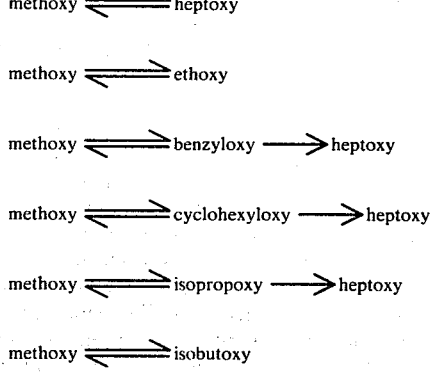

A compound of the formula (II) is reacted with a large excess of an alcohol of the formula (III). In the compounds of the formulae (II) and (III), respectively, the definition of R' and R" is identical, with the proviso that in a given pair of reactants R' and R" are always different. Alcohols of the formula (III) preferably are used in an amount of 30 to 50 molar equivalents related to the compounds of the formula (II).

Reaction of the compounds of the general formula (II) with compounds of the formula (III) is performed in an organic solvent. As a solvent for example ether-type solvents, such as diethylether, tetrahydrofurane, dioxane; chlorinated hydrocarbons, such as dichloromethane, chloroform, carbon tetrachloride or benzene or benzene homologues (toluene, xylene), or other solvents, e.g. ethyl acetate, acetone or dimethyl formamide, or an excess amount of the reactant of the formula (III) are used. Of the above-listed solvents chlorinated hydrocarbons are most preferably used, in the absence of water.

Reaction is accomplished in the presence of an acid, at a pH between 3 and 5. The pH-value is adjusted by mineral acids, e.g. hydrochloric acid, sulfuric acid or a Lewis acid, such as chlorotrifluoride diethyletherate.

The reaction temperature is selected between the freezing point and boiling point of the solvent employed. The reaction is generally carried out at a temperature between −60° C. and +25° C.

When the reaction is complete, the pH of the reaction mixture is adjusted to 8 to 10, for example with an ammonium hydroxide solution or, preferably, with solid potassium carbonate.

The product is isolated from the reaction mixture by extraction and/or evaporation, and if desired it is purified by chromatography and/or crystallization. Chromatography is effected on partially deactivated alumina or fine-grained silica gel.

The present invention is further illustrated by the following non-limiting Examples.

EXAMPLE 1

N-Desmethyl-N-(methoxymethyl)-vinblastine 1.0 g. (1.1 moles) of vinblastine sulfate are dissolved in a mixture of 240 ml. alcohol-free absolute dichloromethane, 8.0 ml. of methanol and 25 ml. of glacial acetic acid. The solution is cooled to −55° C. A solution of 0.5 g. (5.0 mmoles) of chromium trioxide in 40 ml. of acetic anhydride is cooled to −55° C. and is then added dropwise to the vinblastine solution under dry nitrogen atmosphere, with vigorous stirring in 5 minutes. During the addition the temperature of the reaction mixture must not exceed −50° C. The progress of the oxidation reaction is monitored by thin layer chromatography (DC-Alufolien Kieselgel 60 F$_{254}$; 10:0.5:0.5:0.5 mixture of diethyl ether, ethanol, benzene and diethyl amine). Generally the oxidation terminates in 20 to 30 minutes. Thereafter a mixture of 190 ml. of concentrated aqueous ammonium hydroxide solution and 200 g. of ice is added to the reaction mixture under cooling. The temperature raises from −55° C. to a temperature between 0° C. and +10° C. When this temperature is reached outer cooling is terminated and the solution having a pH of 8.5 to 9 is vigorously stirred for 10 minutes. The phases are separated, the aqueous phase is extracted with three 30-ml. portions of dichloromethane, and the extracts are washed with four 25-ml. portions of a 1:1 mixture of water and ammonium hydroxide and then with two 30-ml. portions of water. The organic phase is dried with anhydrous magnesium sulfate, filtered off and the filtrate is evaporated in vacuo. 0.35 g. of a crude product are obtained. The product is purified by chromatography on a column filled with 0.3 g. of alumina having and activity grade II-III in a dichloromethane solution. 6-ml. dichloromethane fractions are collected, which are analysed by thin layer chromatography (DC-Alufolien Kieselgel 60 F$_{254}$, Art. 5554; solvent: 5:0.4 mixture of dichloromethane and methanol; detection: iodine vapour or ultraviolet light of 254 nm).

Fractions containing the same alkaloid are combined and evaporated separately. The desired end product is contained in the 6th to 25th fractions.

Yield: 64% of the named compound, which is chromatographically uniform. M.p.: 205° to 210° C. (ethanol).

$[\alpha]_D^{20} = +23°$ (c=1, chloroform).

$^1$H—NMR (CDCl$_3$, 100 MHz); δ9.05/s, 1H, C$_{16}$—OH/, 8.05/s, 1H, N$_a$,H/, 7.35/s, 1H, C$_{12}$,—H/, 7.13–7.26/m, 3H, C$_9$,—C$_{11}$,—H/, 6.68/s, 1H, C$_9$—H/, 6.33/s, 1H, C$_{12}$—H/, 5.84/d, 1H, C$_{14}$—H/, 5.37/s, 1H, C$_{17}$—H/, 5.28/d, 1H, C$_{15}$—H/, 4.42/2H, >N$_a$—CH$_2$—O—/, 4.18/s, 1H,C$_2$—H, 3.97/s, 3H, C$_{16}$—CO$_2$CH$_3$/, 3.77/s, 3H, C$_{11}$—OCH$_3$/, 3.62/s, 3H, C$_{16}$,—CO$_2$CH$_3$/, 3.26/s, 3H, —OCH$_3$/, 2.73/s, 1H, C$_{21}$—H/, 2.00/s, 3H, OCOCH$_3$/, 0.8–0.96/2t, 6H, C$_{18}$—H$_3$, C$_{18}$,—H$_3$/.

MS m/e: 840 (M+100%), 810, 809, 781, 751, 681, 651, 650, 601, 499, 355, 282, 243, 241, 154, 149.

EXAMPLE 2

N-Desmethyl-N-(isobutoxymethyl)-vinblastine 0.5 g. (0.55 mmoles) of vinblastine sulfate are dissolved in a mixture of 120 ml. of absolute dichloromethane, 3.7 ml. of isobutanol and 12.5 ml. of glacial acetic acid and the solution is cooled to −55° C. 0.25 g. (2.5 mmoles) of chromium trioxide in 40 ml. of glacial acetic acid cooled to −55° C. are then added and the progress of the reaction is monitored by thin layer chromatography as described in Example 1 (DC-Plastikfolien Kieselgel 60 F$_{254}$, Art. 5735; 10:0.5:0.5:0.5 mixture of ether, ethanol, benzene and diethyl amine). The reaction terminates in 140 minutes. Furtheron treating the reaction mixture as described in Example 1 0.65 g. of crude product are obtained. The crude product is purified by column chromatography on a Kieselgel 60 (Art. 9385) adsorbent, in dichloromethane solvent. The column is washed and eluted with dichloromethane. 10-ml. fractions are collected. The first 330 ml. of eluate do not contain any alkaloid. Elution is then continued with dichloromethane containing 3% methanol. The first 90 ml. eluate contains the desired compound, which is isolated by evaporation.

Yield: 169 mg. (35%) of the named compound.

Melting point: 215° to 218° C. (acetone and ether).

IR spectrum (KBr): 3400 (NH,OH), 1730 (CO$_2$CH$_3$), 1605, 1220(cm/OAc). $^1$H—NMR/CDCl$_3$, 100 MHZ/:δ8.1/s, 1H, N$_a$,H/, 7.5/M, 1H, C$_{12}$,—H/, 7.05–7.2/m, 3H, C$_9$,—C$_{11}$,—H/, 6.70/s, 1H, C$_9$—H/, 6.36/s, 1H, C$_{12}$—H/, 5.87/d, 1H, C$_{14}$—H/, 5.37/s, 1H, C$_{17}$—H/, 5.30/d, 1H, C$_{15}$—H/, 4.75, 4.15/2H, J$_{AB}$10 Hz, >N$_a$—CH$_2$—O—/, 4.0/s, 1H, C$_2$—H/, 3.78, 3.75/2s, 6H, CO$_2$CH$_3$/, 3.63/s, 3H, C$_{11}$—OCH$_3$/, 2.75/s, 1H, C$_{21}$H/, 2.1/s, 3H, OCOCH$_3$/, 0.95–0.70/12H, CH$_3$—groups/.

MS m/e: 882 (M$^{30}$, 100%), 864, 851, 823, 810, 779, 751, 723, 651, 650, 514, 355, 346, 329, 154.

EXAMPLE 3

N-Desmethyl-N-(heptoxymethyl)-vinblastine

The procedure described in Example 2 is followed except that 3.7 ml. of isobutanol and replaced by 3.7 ml. of 1-heptanol. Reaction time: about 90 minutes. 4 g. of crude product are obtained from the reaction mixture. Purification is carried out on a Kieselgel 60 (Art 9385) chromatographic column in 30 ml. of dichloromethane. The column is washed and eluted with dichloromethane. 10-ml. fractions are collected. The first 300 ml. do not contain any alkaloid. Elution is continued with dichloromethane containing 3% of methanol. The first 120 ml. eluate contains the desired compound.

Yield: 21% of the named compound.

Melting point: 200° to 205° C. (Acetone/ether).

IR spectrum (KBr): 3450/OH,NH/, 1740/CO$_2$CH$_3$/, 1610, 1220/cm/OAc/. $^1$H—NMR (CDCl$_3$, 100 MHz): δ8.07/s, 1H, N$_a$,H/, 7.52/m, 1H, C$_{12}$,—H/, 7.2–7.02/m, 3H, C$_9$,—C$_{11}$,—H/, 6.70/s, 1H, C$_9$—H/, 6.35/s, 1H, C$_{12}$—H/, 5.85/dd, 1H, C$_{14}$—H/, 5.39/s, 1H, C$_{17}$—H/, 5.30/d, 1H, C$_{15}$—H/, 4.75, 4.15/2H, J$_{AB}$ 10 Hz, >N$_a$—CH$_2$—O—/, 4,0 /s, 1H, C$_2$—H/, 3.80, 3.75 /2s, 6H, CO$_2$CH$_3$/, 3.65/s, 3H, C$_{11}$—OCH$_3$/, 2.75/s, 1H, C$_{21}$—H/, 2.10/s, 1H, OCOCH$_3$/, 0.7–1.0/3t, 9H, CH$_3$-groups/.

MS m/e: 924 M+), 906, 893, 865, 822, 810, 765, 751, 737, 651, 650, 649, 469, 455, 355, 282, 154, 135, 122.

EXAMPLE 4

N-Desmethyl-4-(benzyloxymethyl)-vinblastine

The procedure described in Example 2 is followed but 3.7 ml. of isobutanol are replaced by 4.3 ml. of benzyl alcohol. After 45 minutes 4 ml. of an oily product are obtained, which is then isolated by preparative thin layer chromatography (Kieselgel PF$_{254+366}$; a mixture of 100 ml. of dichloromethane and 8 ml. of methanol).

Yield: 75 mg. (15%) of the named compound.

Melting point: 215° to 218° C. (methylene chloride/ether).

IR spectrum (KBr): 3400/OH, NH/, 1740/CO$_2$CH$_3$/, 1610, 1230/cm/OAc/. $^1$H—NMR/CDCl$_3$, 100 MHz/:δ8.07/s, 1H, N$_a$,H/, 7.52/m, 1H, $C_{12}$,—H/, 7.2–7.08/m, 3H, $C_9$,—$C_{11}$,—H, 3H, aromatic/, 6.75/s, 1H, $C_9$—H/, 6.20/s, 1H, $C_{12}$—H/, 5.85/dd, 1H, $C_{14}$—H/, 5.41/s, 1H, $C_{17}$—H/, 5.30/d, 1H, $C_{15}$—H/, 4.80, 4.20/2H, $J_{AB}$ 10 Hz, >$N_a$—$CH_2$—O—/, 4.40/s, 2H, benzyl—$CH_2$/, 4.00/s, 1H, $C_2$—H/, 3.70, 3.68/2s, 6H, $CO_2CH_3$/, 3.63/s, 3H, $C_{11}$—$OCH_3$/, 2.75/s, 1H, $C_{21}$—H/, 1.0–0.70/2t, 6H, $CH_3$—groups/.

MS m/e: 916 (M+, 100%), 885, 857, 822, 810, 796, 779, 757, 751, 737, 651, 650, 649, 514, 355, 346, 329, 282, 154, 135.

EXAMPLE 5

N-Dexmethyl-N-(methoxymethyl)-vinblastine 5 g. (5.5 mmoles) of vinblastine sulfate are dissolved in 150 ml. of water. The vinblastine base is set free by adding a concentrated aqueous ammonium hydroxide solution (pH=8) and is treated with four 50-ml. fractions of dichloromethane. The dichloromethane solution is dried over sodium sulfate, filtered and the filtrate is evaporated to dryness in vacuo. 4 g. of vinblastine base are obtained, which are then dissolved in a mixture of 1000 ml. of alcohol-free dichloromethane, 120 ml. of acetic acid and 6 ml. of methanol. The solution is cooled to −55° C. To the solution a solution of 2.5 g. (25 mmoles) chromium trioxide in 470 ml. of acetic anhydride cooled to −55° C. is added, in 5 minutes. The reaction mixture is stirred at −55° C. for 45 minutes, whereupon it is added to a mixture of 940 ml. of concentrated aqueous ammonium hydroxide solution and 940 ml. of ice water. The temperature must not exceed 300° C. The phases are separated and the dichloromethane phase is admixed with 1000 ml. of a 1% aqueous hydroxide solution. The organic phase is separated, dried over anhydrous sodium sulfate, filtered and the filtrate is evaporated to dryness in vacuo 3.8 g. of a crude product are obtained. Purification is carried out on a chromatographic column prepared from 230 g. of alumina having an activity grade of II–III (Brockmann) and benzene. The crude product is dissolved in 20 ml. of a 8:2 mixture of benzene and chloroform and is layered on the column. Elution is performed with about 8 liters of a mixture containing benzene and chloroform in the above proportion. 100-ml. fractions are collected, which are analyzed by thin layer chromatography (silicagel; 5:5:5:100 mixture of benzene, ethanol, diethyl amine and diethyl ether). Fractions containing the same substance are combined and evaporated. 2.1 g. of the named compound are obtained.

Yield (after recrystallization from 6 ml. of ethanol): 1.5 g.

The physical characteristics of the product are the same as in Example 1.

EXAMPLE 6

N-Desmethyl-N-(propoxymethyl)-vinblastine

Following the procedure described in Example 5 but using 4.5 ml. of propanol instead of methanol as a reactant, 0.6 g. of the named compound are obtained.

Melting point: 200° to 210° C. (ethanol).

$[\alpha]^{20}$ = +31.2° (c=1, chloroform).

$^1$H—NMR/CDCl$_3$, 100 05/MHz/:δ9.05/s, 1H, $C_{16}$—OH/, 8.06/s, 1H, $N_a$,H/, 7.34/m, 1H, $C_{12}$—H/, 7.34–7.12/m, 3H, $C_9$,—$C_{11}$,—H/, 6.68/s, 1H, $C_9$—H/, 6.35/s, 1H, $C_{12}$—H/, 5.84/dd, 1H, $C_{14}$—H/, 5.36/s, 1H, $C_{17}$—H/, 5.28/d, 1H, $C_{15}$—H/, 4.75, 4.15/2H, $J_{AB}$ 10 Hz, >$N_a$—$CH_2$—O—/, 4.18/s, 1H, $C_2$—H/, 3.78/s, 3H, $CO_2CH_3$/, 3.75/s, 3H, $C_{11}$—$OCH_3$/, 3.62/s, 3H, $CO_2CH_3$/, 2.73/s, 1H, $C_{21}$—H/, 2.09/s, 3H, $OCOCH_3$/, 065–0.94/m, 9H, $CH_3$—groups/.

EXAMPLE 7

N-Desmethyl-N-(methoxymethyl)-vinblastine

Following the procedure described in Example 1 but starting from vinblastine dihydrochloride instead of vinblastine sulfate, the named compound is obtained.

Yield: 28%.

The physical characteristics of the product are identical with those given in Example 1.

EXAMPLE 8

N-Desmethyl-N-(methoxymethyl)-vinblastine

Following the procedure described in Example 1 but using alcohol-free chloroform, dichloroethane or acetone as a solvent instead of dichloromethane, the named compound is obtained.

Yield: 40 to 50% depending on the solvent employed.

The physical characteristics are the same as given in Example 1.

EXAMPLE 9

N-Desmethyl-N-(methoxymethyl)-20′-desoxyleurosidine 60 mg. (0.067 mmoles) of 20′-desoxyleurosidine sulfate prepared by catalytic hydrogenation (Pd/C, methanol) of 3′,4′-anhydrovinblastine and a subsequent conversion into the corresponding sulfate salt, are dissolved in a mixture of 20 ml. of absolute dichloromethane, 1.5 ml. of glacial acetic acid and 0.5 ml. of methanol. The solution is cooled to −55° C. and a solution of 30 mg. (0.3 mmoles) of chromium trioxide in 3.5 ml. of acetic anhydride, cooled to −55° C. is added. The reaction terminates in 60 minutes. To the reaction mixture a mixture of 12 ml. of concentrated aqueous ammonium hydroxide solution and 12 g. of ice is added and the phases are allowed to separate. The aqueous phase is shaken with three 10-ml. portions of dichloromethane. The combined organic phase is washed with two 10-ml. portions of a 1:1 mixture of ammonium hydroxide and water ans subsequently with two 5-ml. portions of water. Drying and evaporation of the organic phase affords 48 mg. of a crude product. Purification is carried out by column chromatography (silica gel 0.040 to 0.063 mm. Merck, Art 9385; solvent: $CH_2Cl_2$ followed by a mixture of 3% methanol and $CH_2Cl_2$). 18 mg. (32%) of the named compound are obtained.

Melting point: 185° to 190° C. (decomp.)

$[\alpha]_D$= +50° (c=1, chloroform).

IR spectrum (KBr): 3400/NH/, 1720/$CO_2CH_3$/, 1610, 1230/cm /OAc/. $^1$H—NMR/CDCl$_3$/: δ7.95/s, 1H, $N_a$,—H/, 7.54/m, 1H, $C_{12}$,—H/, 7.2–7.1/m, 3H, $C_9$,—$C_{11}$,—H/, 6.56/s, 1H, $C_9$—H/, 6.11/s, 1H, $C_{12}$—H/, 5.87/dd, 1H, $C_{14}$—H/, 5.46/s, 1H, $C_{17}$—H/, 5.37/d, 1H, $C_{15}$—H/, 4.72, 4.15/2H, >$N_a$—$CH_2$—O—/, 3.80, 3.75, 3.61 /9H, $CO_2CH_3$/, 2.11/s, 1H, $OCOCH_3$/, 1.0–0.6/6H, $CH_3$—groups/.

By the above chromatographic purification step 46 mg. (22%) of N-desmethyl-N-formyl-20′-desoxyleurosidine can be isolated as a by-product.

Melting point: 205° to 210° C. (decomp.)

$[\alpha]_D$= +54° (c=1, chloroform).

EXAMPLE 10

N-Desmethyl-N-(isobutoxymethyl)-vinblastine 0.80 g. of a crude product prepared according to Example 1, which contains 65% of N-desmethyl-N-(methoxymethyl)-vinblastine are dissolved in a mixture of 50 ml. of dry dichloromethane and 2.4 ml. (25 mmoles) of isobutanol. The solution is cooled to 0° C. and hydrochloric acid in absolute ether is added in nitrogen stream, with stirring, until pH 3. The progress of the reaction is monitored by thin layer chromatography (DC-Alufolien Kieselgel 60 $F_{254}$, Art 5554; solvent: 10:0.5:0.5:0.5 mixture of ether, ethanol, benzene and diethyl amine). The reaction mixture is then added into 2 ml. of a concentrated aqueous ammonium hydroxide solution, the phases are separated and the aqueous phase is extracted with three 5-ml. portions of dichloromethane. The combined extract is washed with three 3-ml. portions of water, whereupon the organic phase is dried with magnesium sulfate, filtered and the filtrate is evaporated. 1.7 g. of a crude product are obtained. The product is dissolved in 25 ml. of dichloromethane and is subjected to column chromatography on a Kieselgel 60 (Art. 9385) column. Elution is started with 120 ml. of dichloromethane and is continued with dichloromethane solutions containing, 1%, 2% and 4% methanol, respectively. The first 290-ml. fraction does not contain any alkaloid. The following 300-ml. fraction contains the named compound.

Yield: 416 mg. of the desired product, which has the same physical characteristics as the product of Example 2.

EXAMPLE 11

N-Desmethyl-N-(heptoxymethyl)-vinblastine

Following the procedure described in Example 10 but using 2.5 ml. (17 mmoles) of 1-heptanol instead of isobutanol and carrying out the t.l.c. measurement on DC-Plastikfolien Kieselgel 60 $F_{254}$, Art. 5735 layers, the named compounds is obtained. The crude product is purified by column chromatography as described in Example 11. The first 310-ml. fraction does not contain any alkaloid. The following 200-ml. fraction contains the desired compound. Yield: 350 mg. The physical characteristics of the product are identical with those of the product of Example 3.

EXAMPLE 12

N-Desmethyl-N-(benzyloxymethyl)-vinblastine

The procedure described in Example 10 is followed, except that instead of 1-heptanol 3.0 ml. (27 mmoles) of benzyl alcohol are used as a reactant. The crude product obtained is purified as described in Example 10. The first 350-ml. fraction does not contain any alkaloid, the following 300-ml. eluate contains the named compound. Yield 320 mg. The physical characteristics of the compound are identical with those given in Example 4.

EXAMPLE 13

N-Desmethyl-N-(isobutoxymethyl)-vinblastine 0.1 g. of a crude product prepared according to Example 1, which contains 65% of N-desmethyl-N-(methoxymethyl)-vinblastine, are dissolved in a mixture of 15 ml. of dichloromethane and 30 to 50 molar equivalents of isobutanol and at 0° C., with stirring, till pH 3 hydrochloric acid in absolute ether is added. When the reaction is complete, potassium carbonate is added to the reaction mixture until the pH is adjusted to 7. The precipitated salt is filtered off and the filtrate is purified by column chromatography, as described in Example 10, after direct evaporation or a partial evaporation in vacuo. Yield: 53% of the named compound, which has the same physical characteristics as the product of Example 2.

The following compounds can be prepared in an analogous way, starting from the suitable starting compounds:

N-Desmethyl-N-(isopropoxymethyl)-vinblastine (yield: 34%).

Melting point: 178° to 182° C. (decomp.)

IR spectrum (KBr): 3400/OH, NH/, 1730/$CO_2CH_3$/, 1610, 1220/cm/OAc/.

$^1$H—NMR/$CDCl_3$, 100 MHz/: δ8.1/s, 1H, $N_a$,—H/, 7.51/m, 1H, $C_{12}$,—H/, 7.2–7.03/m, 3H, $C_9$,—$C_{11}$,—H/, 6.70/s, 1H, $C_9$—H/, 6.35/s, 1H, $C_{12}$—H/, 5.85/dd, 1H, $C_{14}$—H/, 5.38/s, 1H, $C_{17}$—H/, 5.30/d, 1H, $C_{15}$—H/, 4.75, 4.15/2H, $J_{AB}$10 Hz, >$N_a$—$CH_2$—O—/, 4.0/s, 1H, $C_2$—H/, 3.78, 3.75, 3.65/9H, $CO_2CH_3$, $C_{11}$—$OCH_3$/, 2.75/s, 1H, $C_{21}$—H/, 2.1/s, 3H, $OCOCH_3$/, 0.95–0.60/12H, $CH_3$-groups/.

N-Desmethyl-N-(allyloxymethyl)-vinblastine (yield: 55%).

Melting point: 205° to 210° C. (decomp.)

IR spectrum (KBr): 3300/OH, NH/, 1730/$CO_2CH_3$/, 1610, 1220/cm/OAc/.

$^1$H—NMR/$CDCl_3$, 100 MHz/: δ8.05/s, 1H, $N_a$,—H/, 7.50/m, 1H, $C_{12}$,—H/, 7.2–7.08/m, 3H, $C_9$—$C_{11}$,—H/, 6.73/s, 1H, $C_9$—H/, 6.25/s, 1H, $C_{12}$—H/, 6.1–5.85/m, 2H, $C_{14}$—H, $CH_2$=CH—$CH_2$—/, 5.40/s, 1H, $C_{17}$—H/, 5.25–5.10/m, 3H, $C_{16}$—H, $\underline{CH_2}$=CH—$CH_2$—/, 4.74, 4.15/2H, >$N_a$—$CH_2$—O—/, 4.15/d, 2H, $CH_2$=CH—$\underline{CH_2}$—/, 3.70, 3.68, 3.63/9H, $CO_2CH_3$, $C_{11}$—$OCH_3$/, 3.73/s, 1H, $C_{21}$—H/, 2.1/s, 3H, $OCOCH_3$/, 1.0–0.7/2t, 6H, $CH_3$—groups.

N-Desmethyl-N-(cyclohexaloxymethyl)vinblastine (yield: 36%).

Melting point: 175°–180° C. (decomp.)

IR spectrum (KBr): 3400/OH, NH/, 1730/$CO_2CH_3$/, 1610, 1230/cm/OAc/.

$^1$H—NHR/$CDCl_3$, 100 MHz/: δ8.05/s, 1H, $N_a$,H/, 7.5/m, 1H, $C_{12}$,—H/, 7.2–7.0/m, 3H, $C_9$,—$C_{11}$,—H/, 6.72/s, 1H, $C_9$H/, 6.32/s, 1H, $C_{12}$—H/, 5.85/dd, 1H, $C_{14}$—H/, 5.37/s, 1H, $C_{17}$—H/, 5.30/d, 1H, $C_{15}$—H/, 4.72, 4.15/2H, $N_a$—$CH_2$—O—/, 4.05/s, 1H, $C_2$—H/, 3.8, 3.75, 3.68/9H, $CO_2CH_3$, $C_{11}$—$OCH_3$/, 2.1/s, 3H, $OCOCH_3$/, 0.95–0.65/2t, $CH_3$—groups/.

EXAMPLE 14

N-Desmethyl-N-(methoxymethyl)-vinblastine 0.15 g. (0.17 mmoles) of N-desmethyl-N-(isobutoxymethyl)-vinblastine are dissolved in a mixture of 30 ml. of dichloromethane and 1.5 ml. of methanol. The solution is cooled to 0° C. and a solution of hydrochloric acid in absolute ether is added dropwise until the pH is 3. The progress of the reaction is followed by thin layer chromatography (Kieselgel 60 $F_{254}$, Art. 5735; a 20:1:1:1 mixture of ether, ethanol, diethyl amine and benzene). When the reaction is complete, the reaction mixture is neutralized with solid potassium carbonate, the solution is filtered and the filtrate is evaporated in vacuo. Yield: 1.14 g. of the named compound, which has the same physical characteristics as the product of Example 1.

EXAMPLE 15

N-Desmethyl-N-(ethoxymethyl)-vinblastine

A solution of 50 mg. of N-desmethyl-N-(allyloxymethyl)-vinblastine in 10 ml. of absolute dichloromethane and 0.3 ml. of ethanol at 0° C. isacidified to pH 3 with hydrochloric acid in absolute ether. After 5 minutes the solution is neutralized with solid potassium carbonate, the precipitated salt is filtered off. 46 mg. of N-desmethyl-N-(ethoxymethyl)-vinblastine are obtained by evaporating the filtrate.

Melting point: 235° to 238° C.
$[\alpha]_D^{25} = +30.5$ (c=1, chloroform).

EXAMPLE 16

N-Desmethyl-N-(propoxymethyl)-vinblastine

To a solution of 100 mg. of N-desmethyl-N-(heptoxymethyl)-vinblastine in 20 ml. of absolute benzene 1 ml. of n-propyl alcohol are added, whereupon the pH is adjusted to 3 with hydrochloric acid in absolute ether. After 5 to 10 minutes the hydrochloric acid is neutralized with solid potassium carbonate. After filtration and evaporation of the filtrate 90 mg. of N-Desmethyl-N-(propoxymethyl)-vinblastine are obtained. The physical characteristics of the product are identical with those of the product of Example 6.

The reaction ion takes place in an entirely analogous way when using diethyl ether, dioxane, acetone or diethyl acetate as a solvent.

EXAMPLE 17

N-Desmethyl-N-(allyloxymethyl)-vinblastine

A solution of 50 mg. of N-desmethyl-N-(methoxymethyl)-vinblastine in 10 ml. of absolute dichloromethane and 0.5 ml. of allyl alcohol at 0° C. is acidified to pH 3 with a 50% solution of borotrifluoride etherate in absolute ether. After five minutes the solution is neutralized with potassium carbonate and the precipitated salt is filtered off. After evaporation of the filtrate 40 mg. of N-desmethyl-N-(allyloxymethyl)-vinblastine are obtained.

The physical characteristics of the compound are identical with those of the product of Example 13.

We claim:

1. A process for the preparation of a compound of the formula

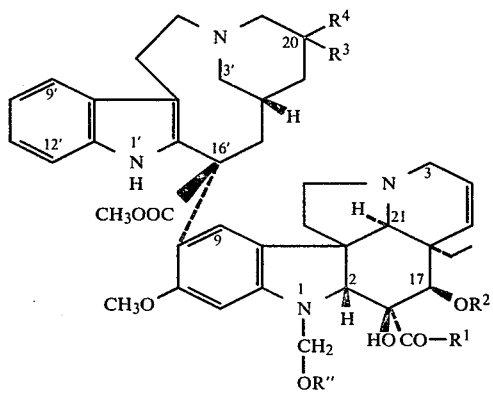

(I)

wherein
$R^1$ is methoxy;
$R^2$ is acetyl;
$R^4$ is $\beta$-hydroxyl and
$R^3$ is $\alpha$-ethyl; or
$R^4$ is hydrogen and
$R^3$ is $\beta$-ethyl;
R" is straight chain alkyl having from 1 to 10 carbon atoms or branched chain alkyl having from 3 to 10 carbon atoms, in which groups the carbon atom attached to the $>N_a$—$CH_2O$— group has a primary or secondary configuration, or alkenyl having from 3 to 6 carbon atoms, alkinyl having from 3 to 6 carbon atoms, cycloalkyl having from 5 to 7 carbon atoms or benzyl, and optionally the epimers thereof, which comprises reacting a compound of the formula

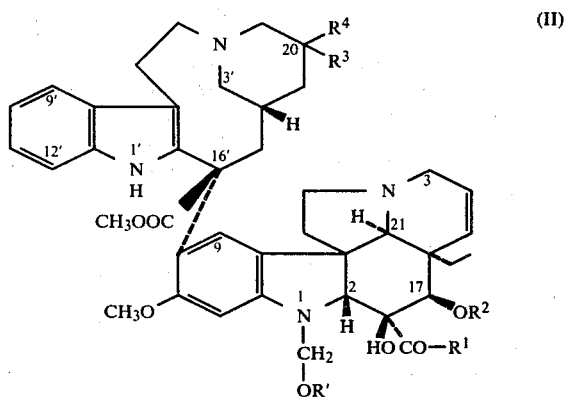

(II)

wherein $R^1$, $R^2$, $R^3$ and $R^4$ are as defined above, R' is a straight chain alkyl having from 1 to 10 carbon atoms or a branched chain alkyl having from 3 to 10 carbon atoms, in which groups the carbon atom attached to the $>N_a$—$CH_2O$— group has a primary or secondary configuration, or alkenyl having from 3 to 6 carbon atoms, alkinyl having from 3 to 6 carbon atoms, cycloalkyl having from 5 to 7 carbon atoms or benzyl, but for a given starting compound of the formula (II) R' is different from R" in a product of the formula (I), prepared therefrom, with a large excess of an alcohol of the formula

 R"—OH (III)

at a pH between 3 and 5, adjusting the pH of the reaction mixture to 7 to 8, isolating a compound of the formula (I) obtained and optionally epimers thereof and if desired, purifying the product.

2. A process as claimed in claim 1, which comprises using 30 to 50 molar equivalents of an alcohol of the formula (III) related to a compound of the general formula /II/.

3. A process as claimed in claim 1 for preparing N-desmethyl-N-(ethoxymethyl)-vinblastine, in which a compound of the general formula (II), wherein R' is as defined in claim 1 except ethyl, $R^1$ is methoxy, $R^2$ is acetyl, $R^3$ is $\alpha$-ethyl and $R^4$ is $\beta$-hydroxyl is reacted with ethanol at pH 3 to 5.

4. A process as claimed in claim 1 for the preparation of N-desmethyl-N-(benzyloxymethyl)-vinblastine, in which a compound of the formula (II), in which R' has the same meaning as defined in claim 1 except benzyl, $R^1$ is methoxy, $R^2$ is acetyl, $R^3$ is $\alpha$-ethyl and $R^4$ is $\beta$-hydroxyl is reacted with benzyl alcohol at pH 3 to 5.

5. A process as claimed in claim 1 for the preparation of N-desmethyl-N-(allyloxymethyl)-vinblastine, in which a compound of the formula (II) wherein R' has the same meaning as defined in claim 1 except allyl, $R^1$ is methoxy, $R^2$ is acetyl, $R^3$ is α-ethyl, $R^4$ is β-hydroxyl, is reacted with allyl alcohol at pH 3 to 5.

6. A process as claimed in claim 1 for the preparation of N-desmethyl-N-(cyclohexyloxymethyl)-vinblastine, in which a compound of the formula (II), wherein R' has the same meaning as defined in claim 1 except cyclohexyl, $R^1$ is methoxy, $R^2$ is acetyl, $R^3$ is α-ethyl, $R^4$ is β-hydroxyl is reacted with cyclohexanol at pH 3 to 5.

* * * * *